United States Patent [19]

Cropper

[11] 4,120,659

[45] Oct. 17, 1978

[54] SULFUR ANALYSIS

[75] Inventor: Wendell P. Cropper, Naperville, Ill.

[73] Assignee: Standard Oil Company (Indiana), Chicago, Ill.

[21] Appl. No.: 813,692

[22] Filed: Jul. 7, 1977

[51] Int. Cl.² ............... G01N 27/06; G01N 31/12
[52] U.S. Cl. ............... 23/230 PC; 422/78; 422/88
[58] Field of Search ........ 23/230 PC, 253 PC, 232 E, 23/254 E

[56] References Cited

U.S. PATENT DOCUMENTS

| | | |
|---|---|---|
| 3,205,045 | 9/1965 | Von Lossberg ............ 23/230 PC X |
| 3,431,770 | 3/1969 | Sanford et al. ............ 23/254 E X |
| 3,547,590 | 12/1970 | Cropper et al. ............ 23/230 PC X |
| 3,838,969 | 10/1974 | Dugan ............ 23/253 PC X |
| 3,880,587 | 4/1975 | Szakasits et al. ............ 23/230 PC |

Primary Examiner—Robert M. Reese
Attorney, Agent, or Firm—Geoffrey M. Novelli; Arthur G. Gilkes; William T. McClain

[57] ABSTRACT

Improved analysis of sulfur concentration in carbonaceous sample uses carbon dioxide produced by the sample as an internal monitor of sample density reflected in the derived sulfur concentration.

5 Claims, 6 Drawing Figures

SULFUR ANALYSIS

BACKGROUND OF THE INVENTION

Heretofore, accurate analysis of the sulfur concentration in hydrocarbon samples has required separate measurement of the sample density. The sulfur analysis technique taught in U.S. Pat. No. 3,547,590 (Cropper et al., 1970), which is specifically incorporated herein by reference, is fully automatic but is nevertheless limited in the speed and convenience with which its readings can be used because they must be corrected by separate density measurement for accuracy desired increasingly. This limitation has been eliminated by the improved sulfur analysis technique claimed herein.

BRIEF SUMMARY OF THE INVENTION

The improved sulfur analysis technique reflects the density of a carbonaceous sample by using the quantity of carbon dioxide produced by oxidation of the sample as a monitor of the sample density. The preferred embodiment comprises use of an aqueous solution of the carbon dioxide to generate a quantitative electrical conductivity signal which is compared to a separate signal generated by sulfur containing solution, to produce a sulfur concentration reading which reflects the density of the sample.

BRIEF DESCRIPTION OF THE DRAWING

FIG. 2 is a representation of a typical recording produced by the apparatus depicted in FIG. 1.

DETAILED DESCRIPTION OF THE INVENTION

While modification of other analytical techniques such as piezoelectric response taught in U.S. Pat. No. 3,431,770 or caustic titration of the two acid gases, could be adapted to accomplish a quantitative comparison of the carbon dioxide and sulfur dioxide produced by oxidation (combustion) of a carbonaceous sample, the preferred technique embodying this invention is to measure the electrical conductivity of separate aqueous solutions of carbon dioxide and sulfur dioxide. Electrical conductivity is a more sensitive and precise measurement from these dilute aqueous solutions than alternatives such as pH measurement, conventional titration, ion specific electrodes or coulometry. This technique can be used to provide sulfur concentration in a variety of carbonaceous materials including petroleum distillates, carbon chemicals, alcohols and similar materials.

PREFERRED EMBODIMENT

Figure 1:
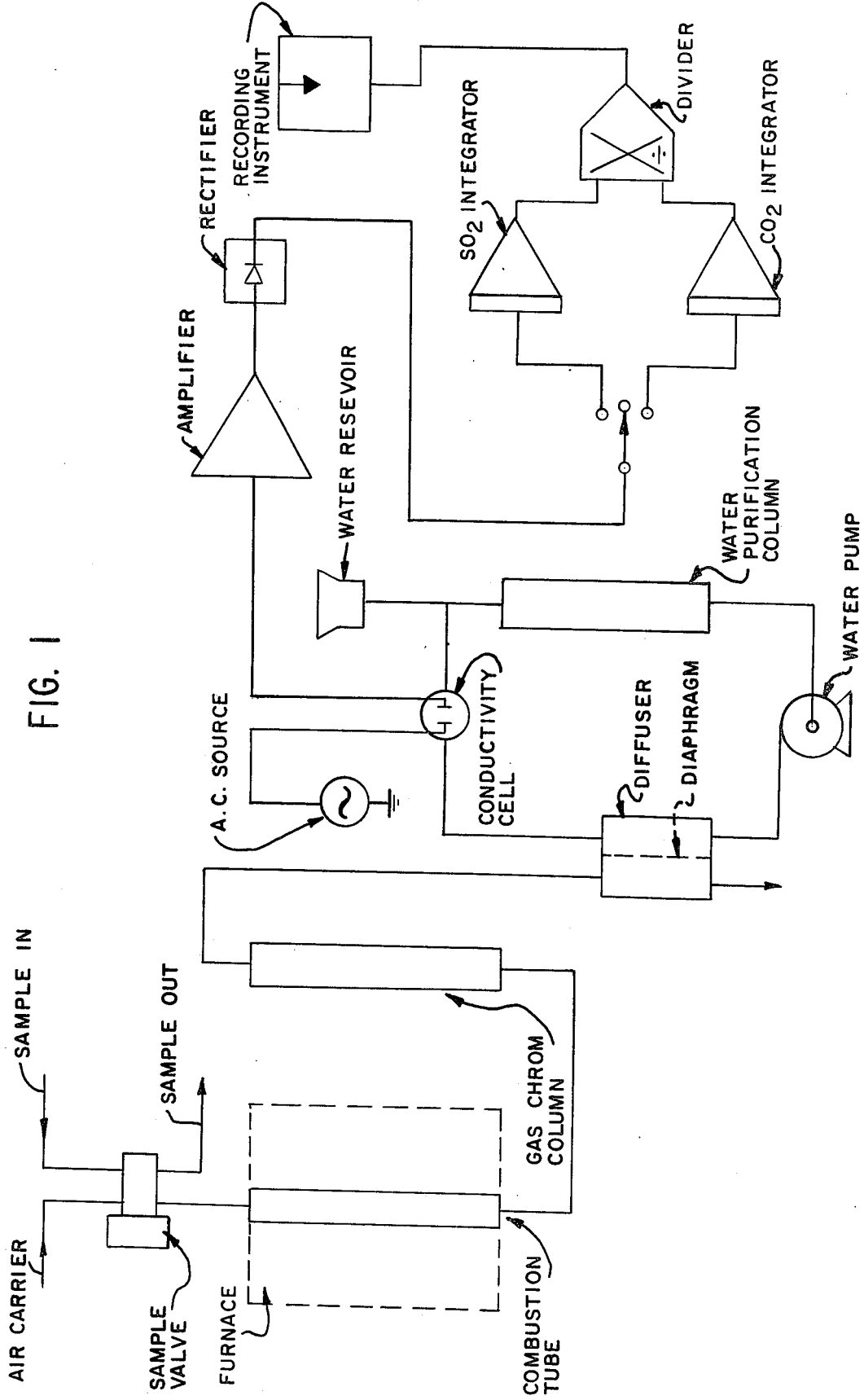
FIG. 1 is a schematic representation of the apparatus embodying this invention in a preferred arrangement.

Successful operation of the improved analyzer has been reliably demonstrated, and FIG. 1 is a depiction of the preferred embodiment but does not indicate limitation upon the scope of the invention or claims. Referring to FIG. 1, a sampling valve is used to extract a 6.5 microliter sample of liquid to be analyzed from a liquid sample stream passing through the valve. The sample is transferred to a carrier air stream which also passes through the sampling valve. The carrier sweeps the sample into a combustion tube maintained at a temperature of 1,500° F. The sample is converted to carbon dioxide, sulfur dioxide and water in the combustion tube. Products of combustion are separated by a gas chromatography (gas chrom) column made from a 2-foot section of ¼ inch stainless steel tubing packed with 40 to 80 mesh silica gel. The gas chrom column temperature is controlled at 205° F. Carrier rate is 900 scc/min.

Carbon dioxide elutes first and is swept by the carrier into a diffusion cell which consists of two Teflon blocks with channels cut into one surface of each block. The channels are placed opposite each other and are separated by a gas permeable Teflon diaphragm. One of the channels is the gas channel through which the gas chrom column effluent passes. Ion-free water is pumped through the other channel in the diffusion cell. Carbon dioxide eluting from the column flows into the gas channel of the diffusion cell and diffuses through the Teflon diaphragm into the water stream flowing in the opposite channel of the diffuser. The carbon dioxide dissolves in the water, producing ions, which increase the electrical conductivity of the water.

Figure 2A:
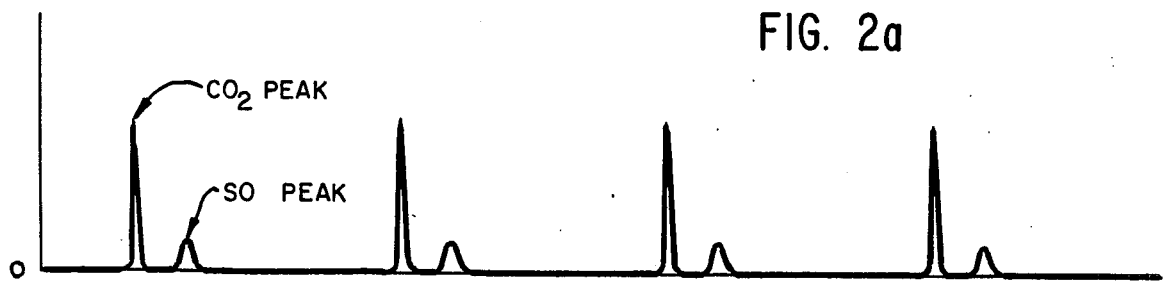
FIG. 2(a) shows peaks typical of gas chrom systems as generated by this detection system.

The increase in electrical conductivity is detected by a conductivity cell, maintained at constant temperature, connected to a 100 Hz source, and an electrical circuit which produces a voltage proportional to conductance of the liquid in the conductivity cell. This detection system generates a Gaussian type peak typical of gas chrom systems depicted in FIG. 2(a). After elution of carbon dioxide is completed, the sulfur dioxide produced in the combustion tube elutes into the gas channel of the diffusion cell and passes through the Teflon diaphragm into the water stream. Ions formed by the dissolved sulfur dioxide increase electrical conductivity of the water and generate a proportional detector signal.

The detector system, therefore, generates electrical signals proportional to the size of the carbon dioxide and sulfur dioxide peaks.

An amplifier and rectifier circuit converts the conductance signals to proportional d.-c. voltages. Not shown is an auto-zero circuit which establishes a baseline for measurement of the carbon dioxide and sulfur dioxide peak areas. The auto-zero circuit is a conventional sample-and-hold circuit based on a Bell and Howell 20-419A tracking module.

Figure 2B:
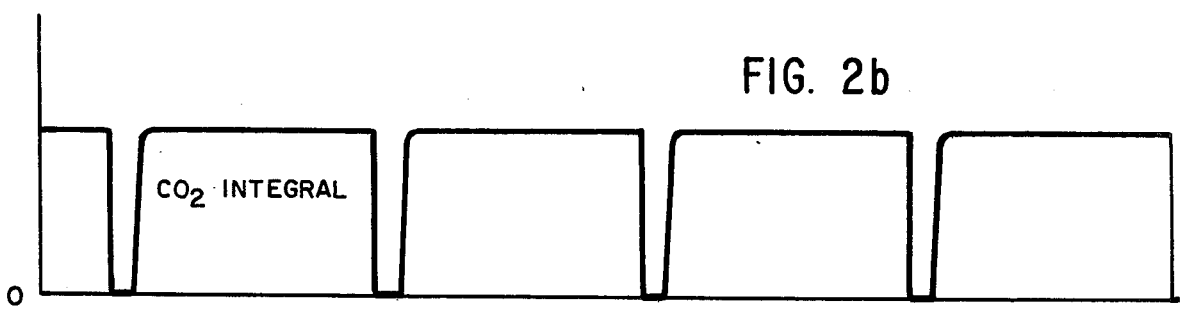
FIGS. 2(b) and 2(c) show integrator voltages proportional to the respective heights of the peaks of FIG. 2(a).
Figure 2C:
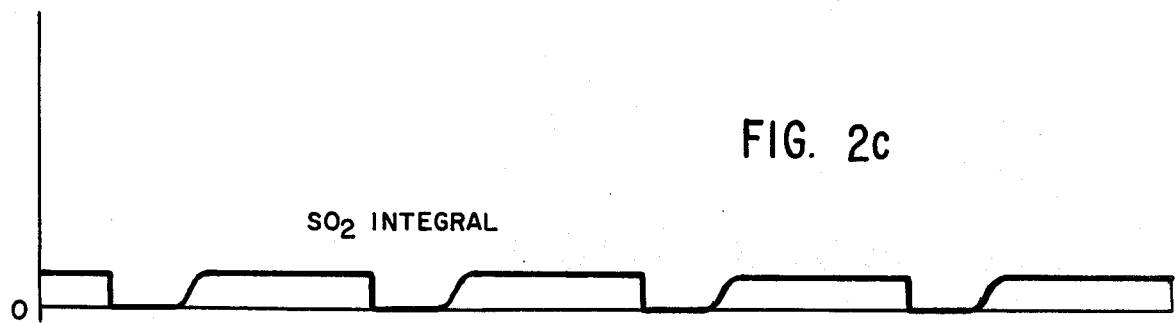

Though a single integrator with memory module could be used, more desirably two conventional integrating circuits with appropriate time constants, are used to measure peak areas. During elution of the carbon dioxide peak, one integrator provides the time integral of the detector peak generated by carbon dioxide. At the appropriate time, the detector signal is switched into a second integrator which provides the time integral of the sulfur dioxide peak. Output of each integrator is a d.-c. voltage proportional to the respective peak sizes as depicted in FIGS. 2(b) and 2(c).

Figure 2D:
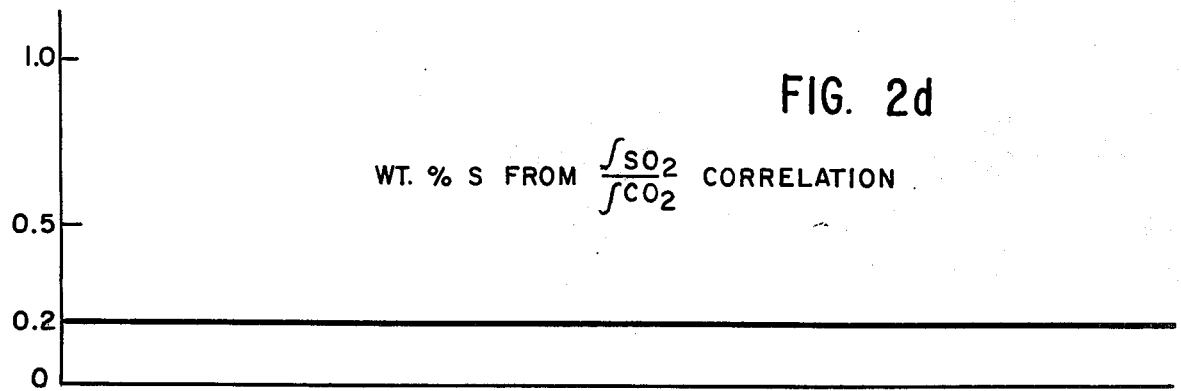
FIG. 2(d) shows an output signal proportional to the ratio of the sulfur dioxide peak size to the carbon dioxide peak size.
Figure 3:
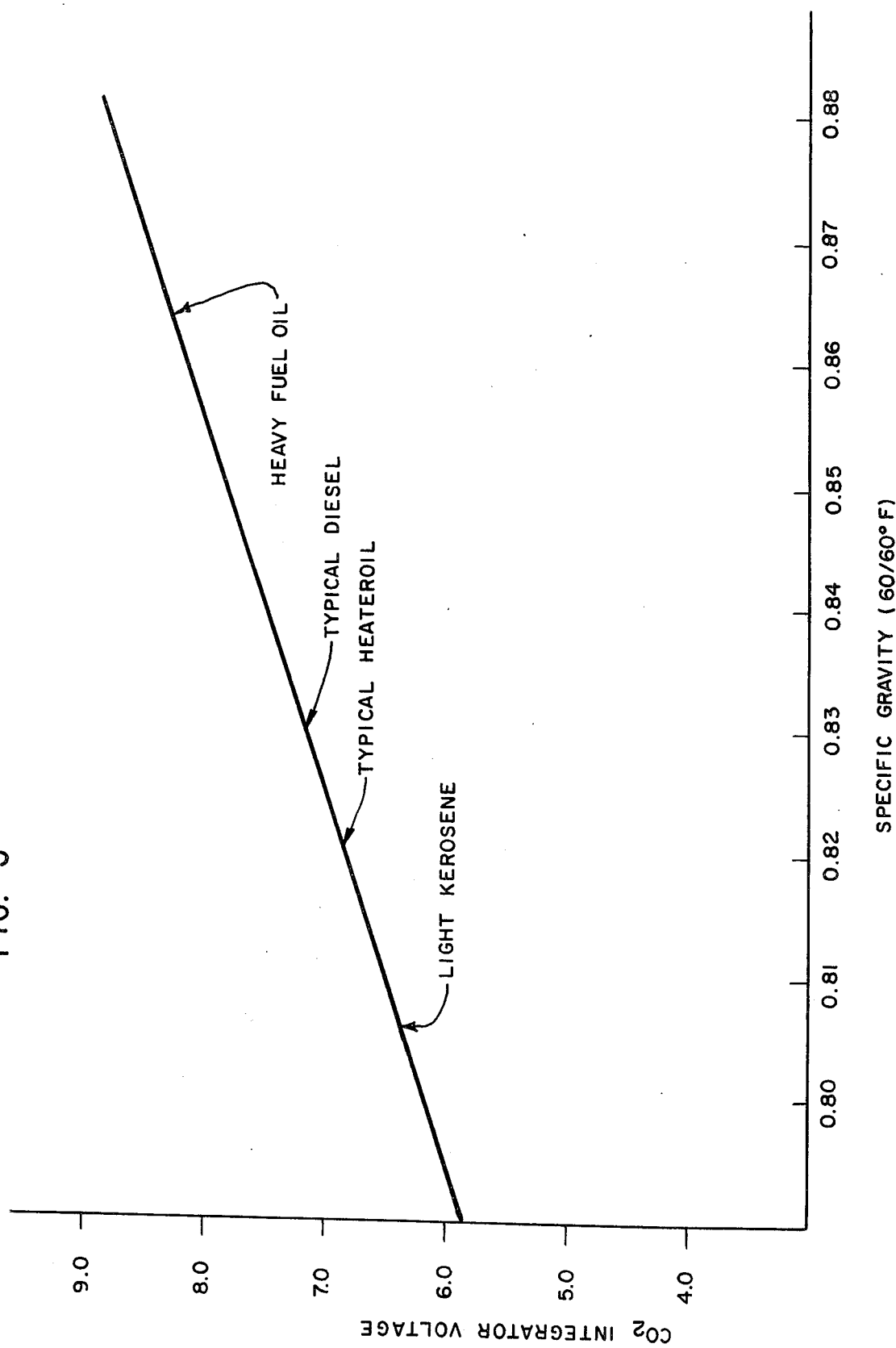
FIG. 3 is a plot showing a correlation of quantitative $CO_2$ (integrator voltage) with density of typical petroleum distillate samples.

The integrator signals are applied to a divider circuit which generates an output signal proportional to the ratio of the sulfur dioxide peak size to the carbon dioxide peak size as depicted in FIG. 2(d). The ratio measurement provides advantages over measurement of the sulfur dioxide peak size and correlation of this measurement with wt. % sulfur as follows:

1. Size of the carbon dioxide peak is directly proportional to weight percent carbon in the sample, therefore the size of the carbon dioxide peak reflects density differences shown in the calibrated correlation of FIG. 3. The character of the materials being analyzed will dictate other calibrations, e.g. for highly aromatic chemicals or alcohols. In contrast, calibration of size of the sulfur dioxide peak with known sulfur level need not be revised for materials of different character when the carbon dioxide monitor is used. The distillate fuel analyzers are frequently used to measure sulfur levels in kerosene, heater oil, furnace oil and Diesel fuel. Usually the instruments are switched among several products and stream density differences affect mass of sample analyzed because the sampling valve, operating at a constant temperature, is designed to take a constant volume sample for analysis. Therefore, larger carbon dioxide peaks are generated by furnace oil than by kerosene. Carbon dioxide integrator output voltages reflect density differences when the instrument is switched amoung the various distillates. In effect, carbon dioxide is used as an internal standard for the gas chrom analysis. The peak ratio measurement therefore is an accurate index of sulfur level in the sample, regardless of sample stream density. This technique obviates the need for a separate on-line density measuring instrument which otherwise would be required for proper interpretation of sulfur analyzer readings.

2. Sample valve variability is effectively eliminated by the ratio techniques.

Advantages of the ratio technique significantly improve accuracy and reliability of on-line sulfur measurements.

All electronic circuits are constructed from commercial circuit modules in design readily apparent to those skilled in analytical instrumentation.

I claim:

1. An improved method for measuring the concentration of sulfur contained in a carbonaceous sample without separate measurement of sample density, comprising oxidation of the sample and separation of oxidation product carbon dioxide from sulfur-containing gas produced by the sample, wherein the improvement comprises:
   (a) measuring the quantity of sulfur-containing gas;
   (b) measuring the quantity of carbon dioxide; and
   (c) taking the ratio of the sulfur-containing gas measurement to the carbon dioxide measurement in order to determine the sulfur concentration using the carbon dioxide as an internal monitor of the sample density.

2. The method of claim 1 comprising:
   (a) diffusing the sulfur-containing gas into water;
   (b) measuring a quantitative signal generated from the sulfur-containing water;
   (c) diffusing the carbon dioxide into water;
   (d) measuring a quantitative signal generated from the carbon dioxide containing water; and
   (e) taking the ratio of the sulfur-containing gas signal to the carbon dioxide signal in order to determine the sulfur concentration using the carbon dioxide as an internal monitor of the sample density.

3. Apparatus for measuring the concentration of sulfur in a carbonaceous sample having oxidation means producing carbon dioxide and sulfur-containing gas, wherein the improvement comprises:
   ratio means for taking the ratio of a quantitative signal generated from the sulfur-containing gas to a quantitative signal generated from the carbon dioxide.

4. The apparatus of claim 3 wherein the ratio means comprises electrical circuitry for taking the ratio of a quantitative signal generated from the sulfur-containing gas to a quantitative signal generated from the carbon dioxide.

5. The apparatus of claim 4 wherein the ratio means comprises one or more integrators and a divider.

* * * * *

UNITED STATES PATENT OFFICE
CERTIFICATE OF CORRECTION

Patent No. 4,120,659      Dated October 17, 1978

Inventor(s) Wendell P. Cropper

It is certified that error appears in the above-identified patent and that said Letters Patent are hereby corrected as shown below:

Claim 6 should be added, as shown in Examiner's Amendment,

Paper No. 5, page 2, as follows:

-- The method of claim 1 wherein said carbonaceous sample comprises petroleum distillate. --.

On the cover sheet "claim 5" should read -- claim 6 --.

Signed and Sealed this

Twelfth Day of June 1979

[SEAL]

Attest:

RUTH C. MASON
*Attesting Officer*

DONALD W. BANNER
*Commissioner of Patents and Trademarks*